United States Patent [19]

Jacquet et al.

[11] 4,425,321
[45] Jan. 10, 1984

[54] DEODORANT COMPOSITIONS CONTAINING A POLYCARBOXYLIC ACID SALT

[75] Inventors: Bernard Jacquet, Antony; Gerard Lang, Epinay-sur-Seine; Alain Malaval, Aulnay-sous-Bois, all of France

[73] Assignee: L'Oreal, Paris, France

[21] Appl. No.: 929,193

[22] Filed: Jul. 28, 1978

[30] Foreign Application Priority Data

Jul. 29, 1977 [FR] France ............................. 77 23507

[51] Int. Cl.³ .......................... A61K 7/32; A61K 7/36
[52] U.S. Cl. ............................... 424/47; 424/DIG. 5; 424/65; 424/67; 424/68; 424/69; 424/287; 424/288; 424/305; 424/312; 424/317; 424/318; 562/508; 562/510
[58] Field of Search ............... 424/287, 288, 47, 317, 424/318, 312, 305, DIG. 5, 65; 562/508, 510

[56] References Cited

U.S. PATENT DOCUMENTS

| | | | |
|---|---|---|---|
| 784,411 | 3/1905 | Merling ............................. | 562/510 |
| 1,693,801 | 7/1927 | Adams et al. ..................... | 562/508 |
| 1,703,186 | 2/1929 | Adams ............................. | 260/413 S |
| 1,873,732 | 8/1932 | Adams ............................. | 260/413 S |
| 2,477,116 | 7/1949 | Cowan et al. ..................... | 260/413 S X |
| 2,560,242 | 7/1951 | Pelton et al. ..................... | 562/510 X |
| 2,648,693 | 4/1952 | Schmerling ....................... | 562/510 X |
| 2,653,167 | 9/1953 | Jansen et al. ..................... | 562/510 |
| 2,813,899 | 11/1957 | Haven, Jr. ......................... | 562/510 |
| 2,816,132 | 12/1957 | Trapp ............................. | 562/508 |
| 2,840,586 | 6/1958 | Inhoffen .......................... | 260/413 L X |
| 2,849,466 | 8/1958 | Isler et al. ....................... | 562/510 X |
| 2,918,494 | 12/1959 | Closson et al. ................... | 562/508 |
| 2,957,933 | 10/1960 | Pommer et al. ................... | 562/510 |
| 2,988,560 | 6/1961 | Schmerlin et al. ................ | 260/413 S |
| 3,006,939 | 10/1961 | Pommer et al. ................... | 260/413 L |
| 3,362,970 | 1/1968 | Patton ............................. | 260/413 S |
| 3,546,281 | 12/1970 | Haeck et al. ..................... | 562/508 |
| 3,637,801 | 1/1972 | Kuder ............................. | 562/510 |
| 3,746,730 | 7/1973 | Marbet ........................... | 260/413 L |
| 3,931,257 | 1/1976 | Pawson .......................... | 260/413 L |
| 3,981,990 | 9/1976 | Kelly et al. ....................... | 424/365 |
| 4,044,043 | 8/1977 | Bernady et al. ................... | 562/508 |
| 4,048,204 | 9/1977 | Lee ............................... | 260/413 L |

FOREIGN PATENT DOCUMENTS

| | | | |
|---|---|---|---|
| 1313738 | 11/1962 | France ............................. | 424/365 |
| 2035802 | 12/1970 | France ............................. | 424/65 |
| 2280394 | 2/1976 | France ............................. | 424/65 |
| 4966 | 7/1969 | South Africa ...................... | 424/65 |

OTHER PUBLICATIONS

Yasuzi et al., Chem. Abs., 1974, vol. 80, pp. 87465d.
Stainets, Chem. Abs., 1972, vol. N, pp. 139346a.
Takashi et al., Chem. Abs., 1976, vol. 84, pp. 114157w.
(9th Collective Formula Index–$C_{36}H_{64}O_4$.
Sagarin, Cosm. Sci. & Tech., 1957, pp. 826, 827 to 830, 1210 & 1211.

Primary Examiner—Dale R. Ore
Attorney, Agent, or Firm—Fleit, Jacobson, Cohn & Price

[57] ABSTRACT

Deodorant compositions containing at least one zinc or magnesium salt of a polyacid of the general formula:

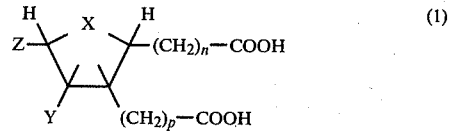

in which X is —CH=CH— or —CHOH—CHOH—, Y is H, a saturated or unsaturated aliphatic radical of 1 to 10 carbon atoms, which is unsubstituted or substituted by one or more hydroxyls, a saturated or unsaturated alicyclic radical of up to 30 carbon atoms, which is unsubstituted or substituted by one or more hydroxyls and/or a carboxylic acid group, or Y denotes a carboxylic acid radical when p=0, Z denotes a saturated or unsaturated hydrocarbon radical of up to 6 carbon atoms, n is an integer less than 10, p is 0 or an integer less than or equal to n, and R is H or a lower alkyl group, and of a positional isomer of such a polyacid, exhibit the advantage that they prevent the development of odors without thereby destroying the biological equilibrium of the skin. The compositions may be in the form of creams, lotions, solids, such as roll-on blocks, sticks or compacted powders, aerosols and the like.

12 Claims, No Drawings

DEODORANT COMPOSITIONS CONTAINING A POLYCARBOXYLIC ACID SALT

DESCRIPTION

The present invention relates to deodorant compositions containing a metal salt as the active principle.

Compositions exist which make it possible to reduce or prevent the formation of unpleasant odours, especially body odour. Such compositions may contain, for example, either compounds which make it possible to suppress the perspiration which is the source of unpleasant body odour, or compounds having a fungicidal action which make it possible to destroy the bacteria which decompose the sweat and thus produce the odour. However, these two methods for suppressing unpleasant odours have considerable disadvantages because they frequently cause skin irritation because of their tanning action and/or destruction of the biological equilibrium of the skin.

Compositions containing, as the active substances, compounds which mask or correct the existing odours are also used, but such compounds have only a very limited effective period.

The use of alkali metal salts of polycarboxylic acids in antiseptic compositions is described, in particular, in French Pat. No. 2,280,394. Such compositions necessarily contain para-halogeno-m-xylenol as an antimicrobial agent. The dicarboxylic acid soaps described in this patent are essentially used for the purpose of solubilising the antimicrobial agents and assisting their action on the bacteria. However, these soaps have no noticeable deodorant action of the type described below.

It has now been discovered that certain metal salts of organic polyacids possess deodorant properties without exhibiting the disadvantages which result from the use of the active substances formerly employed in deodorant compositions. The said metal salt block the development of the odours without thereby destroying the biological equilibrium of the skin. These compounds appear to have an odour-absorbing action by trapping the small molecules, which are responsible for the bad odours, in the crystal lattice formed by the said metal salts of an organic polyacid.

These metal salts also offer the advantage that they are not in the form of sticky waxes, which melt between 30° and 50° C. and are very difficult to handle, as is the case for certain active substances formerly used in deodorant compositions. For the most part, the salts are in the form of a powder which can be ground and obtained in a very fine form without difficulty.

The deodorant compositions according to the present invention are essentially characterised by containing, as an active principle, at least one zinc or magnesium salt of an organic polyacid of the general formula:

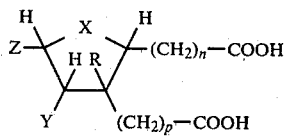

(1)

in which X is —CH═CH— or —CHOH—CHOH—, Y is a hydrogen atom, a saturated or unsaturated aliphatic radical of 1 to 10 carbon atoms which is unsubstituted or substituted by one or more hydroxyls, a saturated or unsaturated alicyclic radical of up to 30 carbon atoms which is unsubstituted or substituted by one or more hydroxyls and/or by a carboxylic acid group, or Y denotes a carboxylic acid radical when p=O, Z denotes a saturated or unsaturated hydrocarbon radical of up to 6 carbon atoms, n is an integer less than 10, which preferably has the value 7 or 8, p is O or an integer which is less than or equal to n, and R is a hydrogen atom or a lower alkyl group, or of a positional isomer of such an acid.

Compounds which are advantgeously used for the purposes of the invention are the zinc or magnesium salts of the dimers or trimers of linoleic or linolenic acid, and also their hydroxyl derivatives.

The following polyacids are more particularly preferred according to the present invention:

(a)
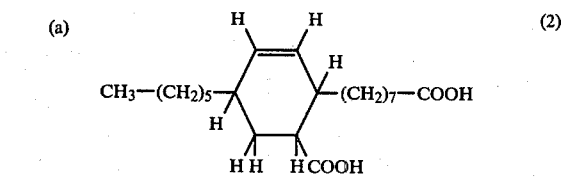
(2)

(b)
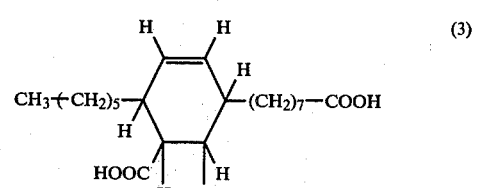
(3)

(c)
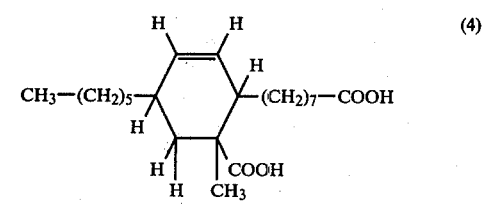
(4)

(d) the dihydroxy acids obtained by careful oxidation of the acids (a), (b) or (c)

(e)
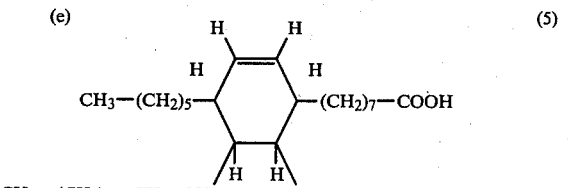
(5)

(f)
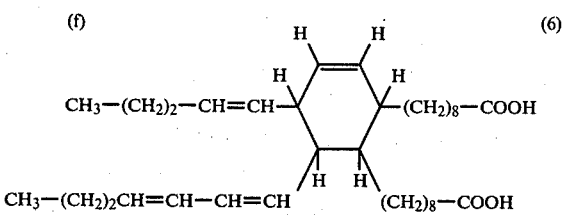
(6)

referred to as dimerginic acid

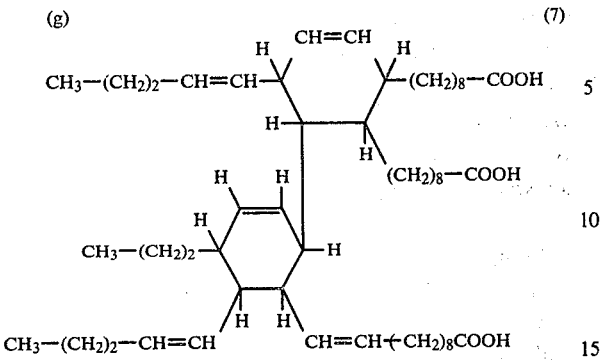

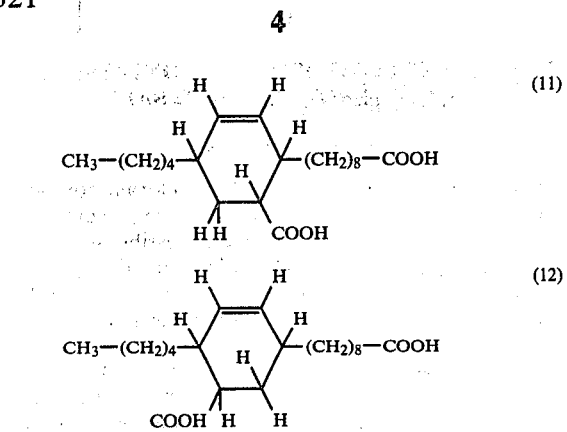

referred to as trimerginic acid (h) the polyhydroxy acids obtained by careful oxidation of the acids (e), (f) or (g), (i) any other acid which is isomeric with the acids (a) to (h) respectively.

The isomers mainly result from the method of preparation of the abovementioned polycarboxylic acids. In fact, the polyacids used in the preparation of the metal salts according to the present invention are obtained by a Diels-Alder reaction of an unsaturated fatty acid with compounds which react as a dienophile.

Thus, for example, acids which are isomeric with the diacid of the formula (2) are understood as meaning various polyacids resulting from the reaction of linoleic acid with a dienophile which is acrylic acid in the case in question.

In fact, as is well known, linoleic acid can isomerise into two conjugated acids corresponding to the following formulae (8) and (9):

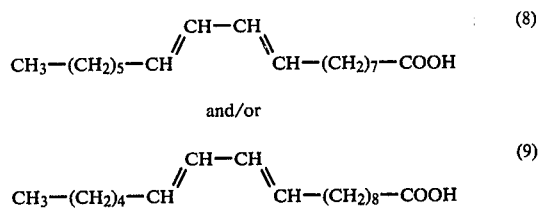

When the compound used as a dienophile, for example acrylic acid, condenses, in accordance with the well-known Diels-Alder reaction, with the conjugated forms (8) and (9) of linoleic acid, the formation of the following polyacids is observed:

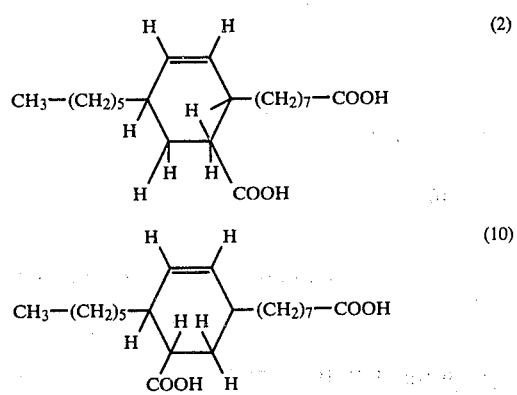

which result from the acid of the formula (8), and:

which result from the acid (9).

The isomers corresponding to the acid described under (2) therefore correspond to the formulae (10), (11) and (12) defined above.

It should be noted that any one of the acids defined in paragraphs (a) to (h) above can be in the form of a mixture of its various isomers which can all be represented in the same manner as that indicated for the polyacid of the formula (2).

The salts are obtained by conventional techniques which employ either a double decomposition reaction of the alkali metal salts of the acids of the formula (1) with zinc or magnesium salts such as the sulphates, chlorides or acetates, or by the direct action of the acids on the corresponding metal oxides such as, for example, magnesia.

The metal salts as defined above can be used as obtained, in the formulations which are generally adopted for deodorant compositions, and, in particular, they can be used in powder form.

The compounds according to the present invention can be employed in formulations which are intended for cosmetic use and they can be employed especially in the form of creams, gels, lotions, solids, such as roll-on blocks, sticks or compacted powders, uncompacted powders, aerosols and the like.

The compounds as defined above can also be used in cleaning products and, in particular, in air fresheners, in products for removing odours from refrigerators, dust-bins and waste-disposal chutes, in products for litters and pet cages and in odour-absorbing products for ventilation ducts in flats.

When the cosmetic compositions according to the invention are in the form of creams or sticks, their formulation can be based on soaps or fatty alcohols in the presence of emulsifiers.

The soaps can be formed from natural or synthetic fatty acids having 12 to 18 carbon atoms, such as lauric acid, myristic acid, palmitic acid, oleic acid, ricinoleic acid, stearic acid and isostearic acid, at concentrations which are preferably between 10 and 30%, and alkalising agents such as sodium hydroxide, potassium hydroxide, ammonia, monoethanolamine, diethanolamine and triethanolamine.

The fatty alcohols can be natural or synthetic alcohols having between 12 and 18 carbon atoms. Alcohols derived from copra fatty acids, myristyl alcohol, cetyl alcohol, stearyl alcohol and hydroxystearyl alcohol, at concentrations of between 5 and 25%, may be more particularly mentioned.

The emulsifiers which can be used in the compositions according to the invention can be anionic or non-ionic surface-active agents. Alcohols, alkylphenols and fatty acids, which are polyoxyethyleneated or polyglycerolated, have a linear fatty chain possessing 8 to 18 carbon atoms and most frequently contain 2 to 15 mols of ethylene oxide, may be more particularly mentioned amongst the non-ionic surface-active agent which can be used according to the invention.

The preferred oxyethyleneated or polyglycerolated fatty alcohols are polyoxyethyleneated oleyl alcohol containing 10 mols of ethylene oxide, oxyethyleneated lauryl alcohol containing 12 mols of ethylene oxide, cetyl alcohol oxyethyleneated with 6 to 10 mols of ethylene oxide, oxyethyleneated cetyl/stearyl alcohol containing 10 mols of ethylene oxide, stearyl alcohol containing 10, 15 or 20 mols of ethylene oxide, polyglycerolated oleyl alcohol containing 4 mols of glycerol and polyoxyethyleneated $C_9$–$C_{15}$ synthetic fatty alcohols containing 5 or 10 mols of ethylene oxide.

Other non-ionic emulsifiers are ethylene oxide/propylene oxide copolymers, products resulting from the condensation of ethylene oxide and propylene oxide with fatty alcohols, polyoxyethyleneated fatty amides, polyoxyethyleneated fatty amines, ethanolamides, fatty acid esters of glycerol, fatty acid esters of sorbitol and fatty amide esters of sucrose, such as glycerol monostearate and polyoxyethyleneated sorbitan monostearate.

Amongst the anionic surface-active agents, there may be mentioned, in particular, alkyl-sulphates which may or may not be oxyethyleneated, and preferably sodium laurylsulphate, ammonium lauryl-sulphate, sodium cetyl-/stearylsulphate, triethanolamine cetyl-/stearyl-sulphate, monoethanolamine lauryl-sulphate, triethanolamine laurylsulphate, the sodium salt of the sulphate half-ester of oxyethyleneated lauryl alcohol (containing, for example, 2.2 mols of ethylene oxide) and the monoethanolamine salt of the sulphate half-ester of oxyethyleneated lauryl alcohol (containing, for example, 2.2 mols of ethylene oxide). These compounds are preferably present in amounts of 3 to 15% by weight.

These creams can also contain polymers such as anionic and/or cationic polymers.

They can also contain, as adjuvants, fatty amides, amongst which there may be mentioned oleyl diethanolamide, copra mono- or di-ethanolamide and stearyl monoethanolamide, at concentrations which can range up to 10% by weight, esters such as the acetate of ethylene glycol monoethyl ether, and fatty acid esters of lower alkanols, such as isopropyl myristate or palmitate, organic or vegetable oils such as light vaseline oil, perhydrosqualene, sweet-almond oil, castor oil, olive oil, groundnut oil, coconut oil, rapeseed oil, palm oil, and self-emulsifying waxes chosen from amongst partially sulphated or oxyethyleneated cetyl/stearyl alcohols.

The compositions can be in the form of an emulsion comprising self-emulsifying glycerol stearate sold under the name IMWITOR 960 K by Messrs. DYNAMIT NOBEL, or emulsions comprising a combination of glycerol monostearate with citric acid esters or with fatty alcohols and lipopeptides or with alkali metal stearates, sold respectively under the names LAMEFORM ZEM, LPM and NSM by Messrs. GRUNAU.

When the compositions are in the form of gels, they contain thickeners in the presence or absence of solvents. Thickeners which can be used are sodium alginate or gum arabic, or cellulose derivatives such as methylcellulose, hydroxymethylcellulose, hydroxyethylcellulose and hydroxypropylcellulose. It is thus possible to obtain a thickener for the compositions by mixing polyethylene glycol with polyethylene glycol stearate or distearate, or by mixing phosphoric acid esters with amides. Other thickeners which are preferred according to the invention are starch, crosslinked polyacrylic acids sold under the trademark Carbopol by GOODRICH CHEMICAL COMPANY, and also the abovementioned polymers.

The thickeners are present in amounts varying between 0.5 and 30% by weight, and preferably between 0.5 and 15% by weight.

The solvents are cosmetically acceptable solvents and, in addition to water, it is possible to use lower alcohols having between 1 and 4 carbon atoms, such as ethanol or isopropanol, polyalcohols such as alkylene glycols like ethylene glycol, diethylene glycol, propylene glycol, dipropylene glycol, polypropylene glycol, butylene glycol and hexylene glycol, glycerol, and glycol ethers such as mono-, di- and tri-ethylene glycol monoalkyl ethers like, for example, ethylene glycol monomethyl ether, ethylene glycol monoethyl ether, ethylene glycol monobutyl ether, diethylene glycol monomethyl ether and diethylene glycol monoethyl ether, mono-, di- and tri-propylene glycol monoalkyl ethers such as propylene glycol monomethyl ether, butylene glycol monoalkyl ethers and polyethylene glycol monoalkyl ethers.

When in the form of a gel or a cream, these compositions can contain silicone derivatives such as polyalkylsiloxanes and, in particular, dimethylpolysiloxanes; examples of such derivatives are products sold under the trademark Rhodorsil by Messrs. RHONE-POULENC.

The preparation of the lotions can be based on the abovementioned solvents and the lotions are preferably anhydrous alcoholic lotions such as those based on ethanol or isopropanol. They can be packaged in spraying devices which are well known in the art and can contain, preferably, the magnesium salt of the compound of the formula (2) and its isomers.

The compositions according to the invention can be in the form of sticks or deodorant roll-on blocks, comprising an emulsifying surface-active agent, a thickener such as those of the type defined above, and also other cosmetically acceptable additives.

The compositions according to the invention can be in the form of an optionally compacted powder. In addition to the metal salts of the polyacids according to the present invention, these powders can contain talc, a dispersing agent such as colloidal silica, and various cosmetic adjuvants used in this kind of formulation, such as zinc oxide and magnesium stearate.

In addition to the compounds according to the present invention, the compact products also contain talc, and other additives such as magnesium carbonate, magnesium stearate and basic aluminium chlorohydrate.

Finally, the compositions according to the invention can be in the form of a dry spray packaged in aerosol containers.

For this purpose, suspensions of the compounds according to the present invention are prepared in a lower alkanol having 1 to 4 carbon atoms, such as ethanol or isopropanol, or a fatty acid ester such as isopropyl palmitate, in the presence of talc, or of an anti-redeposition agent such as silicon dioxide.

The propellent gases used in the aerosol containers can be chosen from amongst carbon dioxide gas, nitrogen, nitrous oxide, volatile hydrocarbons such as butane, isobutane and propane, and halogenated hydrocarbons such as methylene chloride and, preferably, fluorinated hydrocarbons (sold under the name Freon by DU PONT DE NEMOURS) which belong, in particular, to the class of the fluorochlorohydrocarbons such as dichlorodifluoromethane or Freon 12, dichlorotetrafluoroethane or Freon 114 and trichloromonofluoromethane or Freon 11. The propellents can be used by themselves or in combination.

These compositions can of course contain other cosmetic adjuvants which are usually employed in this kind of formulation, such as perfumes, dyestuffs which can be used to colour the composition, preservatives, sequestering agents, softening agents, synergistic agents, and also other surface-active agents or polymers, such as those mentioned above.

The zinc or magnesium salts of the polyacids of the formula (1) are present in amounts which are effective for deodorants and, preferably, in amounts of between 0.5 and 10% by weight and, in particular, between 0.5 and 5% by weight.

The pH of the compositions should be adjusted so that the compositions are compatible with the human epidermis.

Those skilled in the art will also know how to prepare any other deodorant cosmetic composition containing, as the active substance, the metal salts of a polyacid which have been defined above, and also any other composition which has a deodorant effect of the abovementioned type and is for a use which is other than cosmetic.

The process for deodorisation treatment, which also forms part of the present invention, is essentially characterised by the use, in the said treatment, of a composition containing at least one metal salt of a polycarboxylic acid as defined above.

These cosmetic compositions can be applied to the axillary regions of the human body or they can be used as a podological powder for the purpose of deodorising the feet and the clothing of the latter.

The abovementioned compounds having a deodorant action can also be used for treating various supports such as fibrous supports, for example textiles, in order to cause them to act as deodorants. They can be incorporated, for example, into sanitary towels, in accordance with processes which are in themselves known. Thus, the deodorant composition, which is stored in liquid form in a vat situated above the machine for manufacturing the said towels, can be brought by gravity up to one or more nozzles situated above the sheet of wood pulp which passes into the pulp grinder.

The deodorant can also be incorporated in powder form into the said towels, for example by spreading it, by means of vibratory feeders, either over the web of ground wood pulp before wrapping, or over the sheet of wood pulp before it passes into the pulp grinder.

The following examples are intended to illustrate the invention without thereby limiting it.

PREPARATION EXAMPLE 1

Diels-Alder reaction of conjugated and elaidinised methyl linoleate with acrylic acid A mixture of 429 g of conjugated and elaidinised linoleic ester, 212 g of acrylic acid, 290 g of acetic acid, 0.2 g of sulphur and 1.87 g of hydroquinone is heated to 120°–130° C. under nitrogen for 5 hours. The reaction mixture is cooled and taken up in hexane. The polymers precipitate and are filtered off over cellulose acetate. The hexane is driven off in vacuo and the residue is taken up in ethyl acetate. The organic phase is washed several times with water, dried and concentrated. The residue is distilled in vacuo in a metal bath. The fractions distilling below 210° C./0.5 mm Hg are removed. The residue which is recovered is the expected product and comprises a mixture of the monoesters of the compounds of the formulae (2), (10), (11) and (12).

Obtained: 268 g (yield 50%).

Analysis: calculated: C 72.13%, H 10.38%; found: C 72.29%, H 10.10%.

PREPARATION EXAMPLE 2

Saponification of the methyl monoester of the diacid obtained in Example 1

268 g of the methyl monoester of the diacid prepared in accordance with Example 1, 600 ml of methanol and 80 g of potassium hydroxide are heated under reflux for 2 hours 30 minutes. The alcohol is evaporated off in vacuo, the residue is dissolved in water and the solution is treated with animal charcoal and filtered. The aqueous solution is acidified with 20% strength sulphuric acid. The supernatant oil is extracted with ether, dried and concentrated.

220 g (yield 85%) of the diacid, which is a mixture of compounds corresponding to the formulae (2), (10), (11) and (12), are obtained.

Analysis: calculated: C 71.59%, H 10.22%; found: C 71.6%, H 10.08%.

PREPARATION EXAMPLE 3

Preparation of the zinc salt of the diacid of Example 2

25 g of diacid are dissolved in a solution of 5.68 g of sodium hydroxide in 500 ml of water. A solution of 20.42 g of zinc sulphate heptahydrate in 500 ml of water is added at ambient temperature, whilst stirring vigorously. The mixture is allowed to stand for a few hours and filtered, and the solid is washed several times with warm water, drained and dried in vacuo at 100° C.

27.7 g of salt are obtained (yield 94%).

Analysis: calculated: C 60.72%, H 8.19%; found: C 60.84%, H 8.26%.

PREPARATION EXAMPLE 4

Magnesium salt of the diacid of Example 2

275 g of diacid and 45.6 g of hydrated magnesia are stirred in 2.5 liters of a 50/50 mixture of water and alcohol for 48 hours. The solution is filtered and concentrated in vacuo. The residue is washed carefully with hexane and then dissolved in $H_2O$/ethanol and the solution is filtered. The filtrate is evaporated in vacuo and the solid obtained is dried in vacuo.

Obtained: 271.2 g. Yield 95%.

Mg determination with EDTA: theory: 6.48%, found: 6.46% and 6.47%.

PREPARATION EXAMPLE 5

Diels-Alder reaction of methyl linoleate with maleic anhydride

A mixture of 100 g of methyl linoleate, 66 g of maleic anhydride, 150 mg of iodine and 200 mg of hydroquinone is heated at 230° C. for two hours. The crude mixture is dissolved in 800 ml of methanol to which about 40 ml of concentrated sulphuric acid are added. The solution is heated under reflux for about 5 hours, the alcohol is evaporated off in vacuo, the residue is taken up in ethyl acetate and the solution is washed with water. The organic phase is dried over sodium sulphate and concentrated in vacuo. The residue is distilled in vacuo and the fractions distilling below 210° C./0.05 mm Hg are removed. The residue is dissolved in a solution of 40 g of potassium hydroxide in 500 ml of ethanol and the whole is heated under reflux for two hours. The alcohol is evaporated off in vacuo and the residue is taken up in water. The acid is liberated by adding 20% strength sulphuric acid and extracted with ethyl acetate. After drying over sodium sulphate, and solvent is removed by distillation in vacuo.

Obtained: 55.4 g. Yield 37.5%.

Analysis: calculated: C 66.64%, H 9.15%; found: C 66.77%, H 9.01%.

The product obtained is a mixture of the acid of the formula (3) and its position isomers.

The salts are obtained as described above.

PREPARATION EXAMPLE 6

Oxidation of the double bond of the diacid of Example 2

12.25 g of potassium permanganate dissolved in 1 liter of water are added, at 0° C., to a solution of 25 g of diacid and 33.5 g of potassium hydroxide in 500 ml of water. The mixture is stirred for 1 hour 30 minutes at 0°–5° C. The manganese dioxide is filtered off over cellulose acetate. The filtrate is acidified with 20% strength sulphuric acid and extracted with ethyl acetate. The organic phase is dried and concentrated.

22 g of $C_{21}$ diol-diacid are obtained (yield 80%).

Analysis: calculated: C 65.28%, H 9.84%; found: C 65.26%, H 9.67%.

The salts are obtained as described above.

PREPARATION EXAMPLE 7

Hydroxylation of linoleic acid dimer (dimerginic acid)

100 g of dimerginic acid are dissolved in a solution of 158 g of potassium hydroxide in 3 liters of water. 57 g of potassium permanganate dissolved in 1 liter of water are then added and the mixture is stirred for 4 hours. The whole is filtered through cellulose acetate and the filtrate is decolorised with dilute hydrogen peroxide. The solution is acidified with 20% sulphuric acid and extracted with ethyl acetate. The organic phase is washed with water, dried over sodium sulphate and evaporated in vacuo.

Obtained: 83 g. Yield 75%.

Iodine number: 28.8.

Acid number: 215.

PREPARATION EXAMPLE 8

Preparation of the zinc salt of dimerginic acid 30 g of dimerginic acid (Hamburger Fettchemie) are dissolved, under the action of heat, in a solution of 4.28 g of sodium hydroxide in 250 ml of water. The clear mixture thus obtained is run slowly into a solution of 15.38 g of zinc sulphate heptahydrate in 400 ml of water. The salt precipitates during this addition. Stirring is continued for a further 1–2 hours and the precipitate is washed with water and dried in vacuo over $P_2O_5$.

32.7 g of product are obtained.

Zinc determination: theory: 10.49%, found: 11.02%.

PREPARATION EXAMPLE 9

Preparation of the zinc salt of hydroxylic dimerginic acid 20 g of the polyhydroxylic acid prepared in accordance with Example 7 are dissolved, under the action of heat, in a solution of 3.07 g of sodium hydroxide in 150 ml of water. The clear mixture is run into a solution of 11.03 g of zinc sulphate heptahydrate in 300 ml of water. The expected salt is isolated in the same manner as previously.

20.9 g are obtained.

Zinc determination: theory: 12.5%, found: 11.7%.

PREPARATION EXAMPLE 10

Preparation of the zinc salt of hydroxylic trimerginic acid.

Preparation of polyhydroxytrimerginic acid

This preparation is carried out using 100 g of trimerginic acid (Hamburger Fettchemie) dissolved in 2 liters of 3 N potassium hydroxide solution. The solution is cooled and a solution of 96.5 g of potassium permanganate in 4 liters of water is added slowly. The reaction is then carried out in the same manner as for dimerginic acid.

100 g of product are obtained.

Iodine number = 35.9.

Acid number = 188.

Preparation of the salt

The method of operation is identical to that described in Preparation Example 8 or 9.

21 g are obtained starting from 33 g of polyhydroxylic trimerginic acid and 15.3 g of zinc sulphate heptahydrate.

Zinc determination: found: 12.9%, theory: 9.9%.

PREPARATION EXAMPLE 11

Preparation of the magnesium salt of dimerginic acid 30 g of dimerginic acid and 3.12 g of $Mg(OH)_2$ are suspended in 500 ml of a 50/50 mixture of ethanol and water. The mixture is stirred for 25–30 hours and then concentrated in vacuo and the residue is washed with alcohol.

The salt is dried in vacuo at 100° C.

24.7 g are obtained.

Magnesium determination: theory: 4.27%; found: 4.21%.

PREPARATION EXAMPLE 12

Preparation of the magnesium salt of the hydroxylic $C_{21}$ diacid (diacid of Example 6)

40 g of hydroxylic $C_{21}$ diacid and 6.1 g of $Mg(OH)_2$ in 600 ml of water are heated under reflux for 6 hours. 300 ml of ethanol are then added and the mixture is heated until the oil formed dissolves.

The mixture is then filtered whilst hot and evaporated to dryness, the residue is taken up in hexane and the solution is filtered.

34 g of the expected product are obtained by concentrating to dryness.

Magnesium determination: theory: 5.95%, found: 6.3%.

COMPOSITION EXAMPLES

EXAMPLE 1

A transparent deodorant roll-on block is prepared in accordance with known techniques by using:
Cationic cellulose sold by Union Carbide under the name "JR 400": 1.0 g
Compound of Preparation Example 4: 4.0 g
96° strength ethanol: 40.0 g
Perfume: 0.8 g
Water: 54.2 g

EXAMPLE 2

A deodorant gel based on the following compounds is prepared:
Stearic acid, triple-pressed: 5.0 g
Propylene glycol: 40.0 g
Pure glycerol: 19.3 g
Sodium hydroxide pellets: 0.83 g
Nonylphenol containing 9 mols of ethylene oxide: 1.60 g
Compound of Preparation Example 4: 4.0 g
Perfume: 0.8 g
Water, q.s.p.: 100 g

EXAMPLE 3

A deodorant cream is prepared by using the following compounds:
Polyoxyethyleneated cetyl/stearyl alcohol (15 mols of ethylene oxide): 12.0 g
Cetyl palmitate: 4.0 g
Isopropyl myristate: 3.0 g
Dimethylpolysiloxane: 0.5 g
Methyl para-hydroxybenzoate: 0.2 g
Propylene glycol: 2.0 g
Compound of Preparation Example 4: 4.0 g
Perfume: 0.5 g
Water: 73.8 g

EXAMPLE 4

The following solution is prepared:
Compound of Preparation Example 4: 4.0 g
96° strength ethanol: 58.0 g
Water: 37.5 g
Perfume: 0.5 g
This solution is used in a spray deodorant.

EXAMPLE 5

A dusting talc is prepared by using the following compounds:
Luzenac Italian variety talc: 80.0 g
Zinc oxide: 3.0 g
Magnesium stearate: 5.0 g
Colloidal silica: 1.0 g
Zinc salt of the compound of Preparation Example 6: 10.0 g
Perfume: 1.0 g

EXAMPLE 6

A deodorant roll-on block is prepared by using the following compounds:
Oleyl/cetyl alcohol oxyethyleneated with 25 mols of ethylene oxide: 2.5 g
Ethylenediaminetetraacetic acid: 0.1 g
Methyl para-hydroxybenzoate: 0.04 g
Dimethylpolysiloxane: 0.2 g
Wheat starch: 4.0 g
Compound of Preparation Example 4: 4.0 g
Perfume: 0.5 g
Water: 88.66 g

EXAMPLE 7

The following compounds are mixed:
Magnesium carbonate: 3.0 g
Magnesium stearate: 2 g
Talc: 66 g
Compound of Preparation Example 3: 10 g
Aluminium chlorohydrate: 17.5 g
Perfume: 1.5 g
The mixture is compacted in accordance with the techniques which are usually employed for forming a deodorant compact.

EXAMPLE 8

The following composition is prepared:
Compound of Preparation Example 3: 1.0 g
Talc: 2.0
Ethanol: 2.5
Perfume: 0.2
This composition is packaged in an aerosol container in the presence of the mixture of gas:
Freon 11 (F 11=trichloromonofluoromethane): 56.6 g
Freon 12 (F 12=dichlorodifluoromethane): 37.7 g

EXAMPLE 9

The following composition is prepared:
Compound of Preparation Example 3: 1 g
Talc: 2.0
Isopropyl palmitate: 2.5
Perfume: 0.3
This composition is packaged in an aerosol container in the presence of the following mixture of propellant gas:
Freon 11: 56.6
Freon 12: 37.7

EXAMPLE 10

The following composition is prepared:
Zinc salt of the compound of Preparation Example 6: 1.0 g
Silicon dioxide: 2.8
Isopropyl palmitate: 3.8
Perfume: 0.4
This composition is packaged in an aerosol container in the presence of the following mixture of propellent gas:
Methylene chloride: 32.2
Isobutane/butane/propane (75/14/11): 59.8

On applying the composition defined in any one of the preceding Examples 1 to 10 to the axillary region of the body, which normally produces body odour, a prolonged deodorisation is found in these regions.

In particular, the odour-absorbing activity of the compounds according to the present invention is determined by studying their absorption with respect to butylamine and ethyl mercaptan. A substantial absorption of the odourous product is found in all cases for the various compounds tested.

EXAMPLE 11

A dusting talc is prepared by using the following compounds:
Luzenac Italian variety talc: 80.0 g
Zinc oxide: 3.0 g Magnesium stearate: 5.0 g
Colloidal silica: 1.0 g
Compound of Preparation Example 11: 10.0 g
Perfume: 1.0 g As above, it is noticed that this product absorbs odours.

On applying the powder to the axillary region of the body, a prolonged deodorisation is found.

EXAMPLE 12

The following compounds are mixed:
Magnesium carbonate: 3.0 g
Magnesium stearate: 2.0 g
Talc: 66 g
Compound of Preparation Example 10: 10 g
Aluminium chlorohydrate: 17.5 g
Perfume: 1.5 g The mixture is compacted in accordance with the techniques which are usually employed for forming a deodorant compact.

EXAMPLE 13

The following composition is prepared:
Compound of Preparation Example 8: 1.0 g
Talc: 2.0 g
Ethanol: 2.5 g
Perfume: 0.2 g This composition is packaged in an aerosol container in the presence of the mixture of gas:
Freon 11 (F 11=trichloromonofluoromethane): 56.6 g
Freon 12 (F 12=dichlorodifluoromethane): 37.7 g

EXAMPLE 14

The following composition is prepared:
Compound of Preparation Example 9: 1 g
Talc: 2.0 g
Isopropyl palmitate: 2.5 g
Perfume: 0.3 g This composition is packaged in an aerosol container is the presence of the following mixture of propellent gas:
Freon 11: 56.6
Freon 12: 37.7

When applied to the axillary region of the body by spraying, this composition makes it possible to observe a prolonged deodorisation.

EXAMPLE 15

The following composition is prepared:
Compound of Preparation Example 12: 1.0 g
Silicon dioxide: 2.8 g
Isopropyl palmitate: 3.8 g
Perfume: 0.4 g This composition is packaged in an aerosol container in the presence of the following mixture of propellent gas:
Methylene chloride: 32.2 g
Isobutane/butane/propane (75/14/11): 59.8

Results which are similar to those found previously are obtained by replacing the compounds used in Examples 11 and 15 above by the zinc salts of hydroxylic trimerginic acid, the magnesium salts of dimerginic acid, the zinc salts of hydroxylic dimerginic acid, the zinc salts of dimerginic acid and the magnesium salts of the hydroxylic $C_{21}$ diacid.

We claim:

1. Deodorant composition comprising at least one zinc or magnesium salt of a polyacid of the general formula:

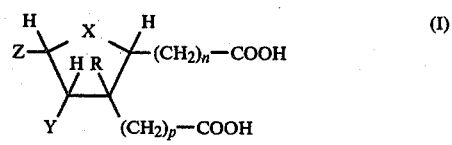

in which X is —CH=CH— or CHOH—CHOH—, Y is a hydrogen atom, saturated or unsaturated aliphatic radical of 1 to 10 carbon atoms, which is unsubstituted or substituted by one or more hydroxyls, a saturated or unsaturated alicyclic radical of up to 30 carbon atoms which is unsubstituted or substituted by one or more hydroxyls and/or by a carboxylic acid group, or Y denotes a carboxylic acid radical when p=O, Z denotes a saturated or unsaturated hydrocarbon of up to 6 carbon atoms, n is at integer less than 10, p is 0 or an integer less than or equal to n, and R is a hydrogen atom or a lower alkyl group, or of a positional isomer of such a polyacid and a cosmetically acceptable carrier.

2. A composition according to claim 1, comprising a magnesium or zinc salt of a dimer or trimer of linoleic or linolenic acid.

3. A composition according to claim 1 in which the said salt is a salt of a polyacid which has the formula:

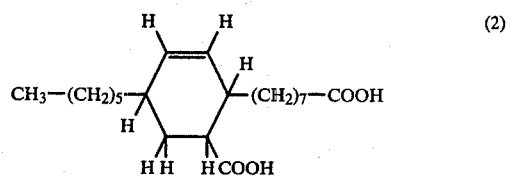

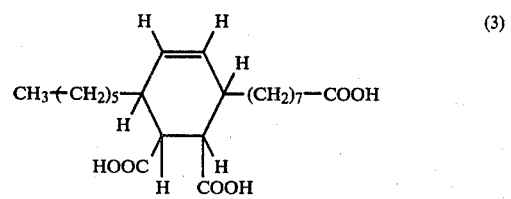

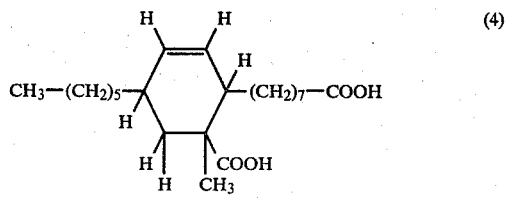

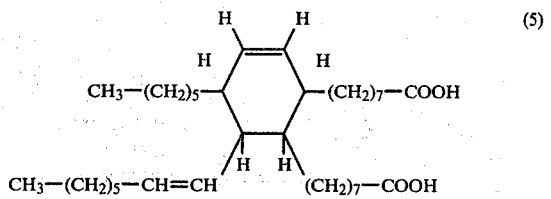

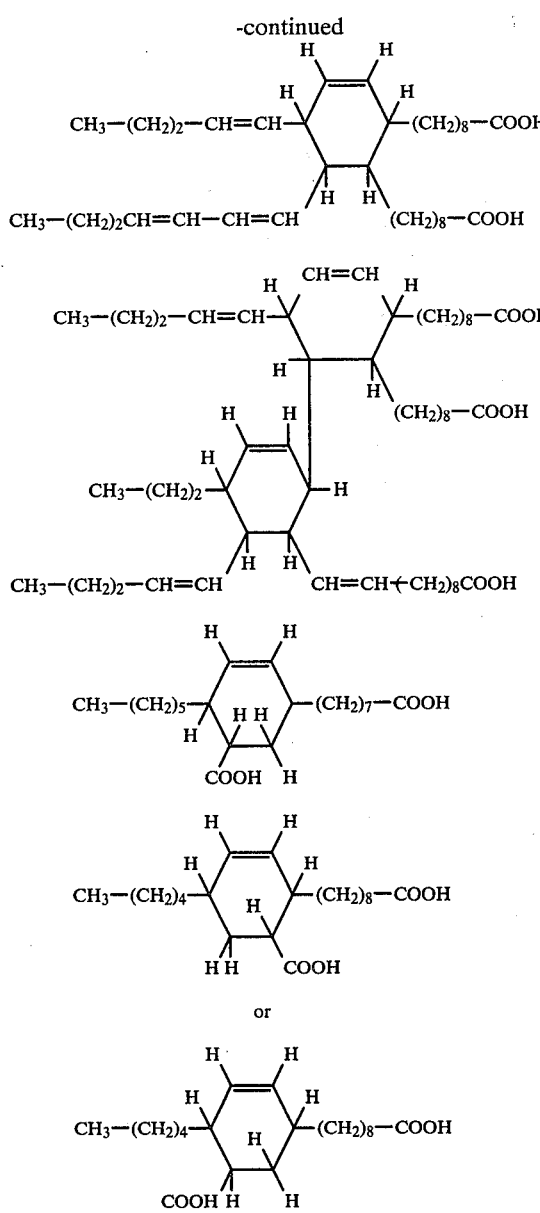

or the polyhydroxy acid oxidation product a said polyacid.

4. A composition according to claim 1, in which the said salt is present in an amount of between 0.5 and 10% by weight.

5. A composition according to claim 1, in the form selected from the group consisting of a cream, a gel, a lotion, a compacted powder, a roll-on block, a roll-on stick, and an aerosol.

6. A composition according to claim 1, which further comprises a soap derived from a substance selected from the group consisting of a fatty acid, a natural alcohol of 12 to 18 carbon atoms, a synthetic alcohol of 12 to 18 carbon atoms, and a fatty alcohol of 12 to 18 carbon atoms and an anionic or non-ionic emulsifier selected from the group consisting of polyglycerolated and polyoxyethyleneated alcohols, alkylphenols, fatty acids, and other adjuvants selected from the group consisting of fatty amides, fatty acid esters, anionic and cationic polymers and cosmetically acceptable oils and waxes and mixtures thereof.

7. A composition according to claim 1, which further comprises a substance selected from the group consisting of a dispersing agent, talc, zinc oxide, silicon dioxide, magnesium carbonate, magnesium stearate and aluminium chlorohydrate.

8. A composition according to claim 1, which contains a cosmetically acceptable solvent and a thickener.

9. A composition according to claim 1, in the form of a lotion containing a lower alcohol and the magnesium salt of the compound, and of a positional isomer thereof, having the formula

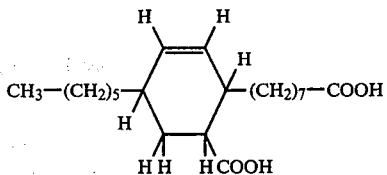

10. A composition according to claim 1 in the form of a suspension in a cosmetically acceptable solvent and a propellant which is packaged in an aerosol container.

11. Deodorant composition comprising at least one zinc or magnesium salt of a polyacid of the general formula:

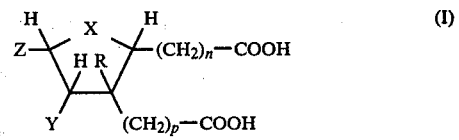

in which X is —CH=CH— or CHOH—CHOH—, Y is a hydrogen atom, saturated or unsaturated aliphatic radical of 1 to 10 carbon atoms, which is unsubstituted or substituted by one or more hydroxyls, a saturated or unsaturated alicyclic radical of up to 30 carbon atoms which is unsubstituted or substituted by one or more hydroxyls or by a carboxylic acid group, or Y denotes a carboxylic acid radical when p=O, Z denotes a saturated or unsaturated hydrocarbon of up to 6 carbon atoms, n is an integer less than 10, p is O or an integer less than or equal to n, and R is a hydrogen atom or a lower alkyl group, or of a positional isomer of such a polyacid, and a carrier selected from the group consisting of a cream including an emulsifier and a soap or a fatty alcohol, a gel containing a thickener, a lotion containing a substance selected from the group consisting of lower alcohols having from one to four carbon atoms, alkylene glycols, and glycol ethers, a compacted powder containing a dispersing agent, and an aerosol packaged dry spray including a propellant agent.

12. A method of reducing or preventing odor, especially body odor comprising the step of applying, to an odiferous or potentially odiferous zone, an effective amount for reducing odor of a deodorant composition comprising at least one zinc or magnesium salt of a polyacid of the general formula:

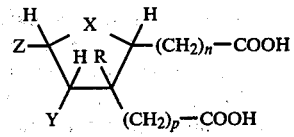

in which X is —CH=CH— or CHOH—CHOH—, Y is a hydrogen atom, saturated or unsaturated aliphatic radical of 1 to 10 carbon atoms, which is unsubstituted or substituted by one or more hydroxyls, a saturated or unsaturated alicyclic radical of up to 30 carbon atoms which is unsubstituted or substituted by one or more hydroxyls or by a carboxylic acid group, or Y denotes a carboxylic acid radical when p=O, Z denotes a saturated or unsaturated hydrocarbon of up to 6 carbon atoms, n is an integer less than 10, p is O or an integer less than or equal to n, and R is a hydrogen atom or a lower alkyl group, or of a positional isomer of such a polyacid and a cosmetically acceptable carrier.

* * * * *